(12) United States Patent
Sumpf et al.

(10) Patent No.: US 10,416,081 B2
(45) Date of Patent: Sep. 17, 2019

(54) OPTICAL SYSTEM AND METHOD FOR SPECTROSCOPY

(71) Applicant: Forschungsverbund Berlin e.V., Berlin (DE)

(72) Inventors: Bernd Sumpf, Wildau (DE); Martin Maiwald, Berlin (DE)

(73) Assignee: Forschungsverbund Berlin e.V., Berlin (DE)

( * ) Notice: Subject to any disclaimer, the term of this patent is extended or adjusted under 35 U.S.C. 154(b) by 0 days.

(21) Appl. No.: 15/725,448

(22) Filed: Oct. 5, 2017

(65) Prior Publication Data

US 2018/0095040 A1 Apr. 5, 2018

(30) Foreign Application Priority Data

Oct. 5, 2016 (DE) .................. 10 2016 118 898

(51) Int. Cl.
*G01N 21/65* (2006.01)
*G01N 21/53* (2006.01)
(Continued)

(52) U.S. Cl.
CPC ......... *G01N 21/65* (2013.01); *G01N 15/1434* (2013.01); *G01N 15/1459* (2013.01);
(Continued)

(58) Field of Classification Search
CPC ............................... G01N 21/65; G01N 15/14
See application file for complete search history.

(56) References Cited

U.S. PATENT DOCUMENTS 4,489,239 A * 12/1984 Grant .................. G01N 21/39
250/338.5
5,422,691 A 6/1995 Ninomiya et al.
(Continued)

FOREIGN PATENT DOCUMENTS

DE      19948391      4/2001
DE      112004001972  8/2006

OTHER PUBLICATIONS

Maiwald et al., "Dual-Wavelength Y-Branch Distributed Bragg Reflector Diode Laser at 785 Nanometers for Shifted Excitation Raman Difference Spectroscopy;" Appl. Spectrosc. 69, 1144-1151 (2015).*

(Continued)

*Primary Examiner* — Shawn Decenzo
(74) *Attorney, Agent, or Firm* — Ray Quinney & Nebeker P.C.; Paul N. Taylor (57) ABSTRACT

Optical systems and methods for spectroscopy are described. The optical system may be particularly suitable for Raman spectroscopy and includes a multispectral excitation source, designed to emit monochromatic excitation radiation successively at at least two different excitation wavelengths along a common beam axis; an elongated flow volume with a longitudinal axis, designed to direct a particle flow along the longitudinal axis; an excitation beam path, designed to irradiate the monochromatic excitation radiation into the flow volume at a first position and the second position that are located in the flow volume and the first position is spaced apart from the second position; and a detection device, designed to wavelength-selectively filter and detect a portion of a radiation scattered from the first position at a first filter wavelength and to wavelength-selectively filter and detect a portion of a radiation scattered from the second position at a second filter wavelength.

18 Claims, 9 Drawing Sheets

(51) Int. Cl.
*G01N 15/14* (2006.01)
*G01N 15/10* (2006.01)

(52) U.S. Cl.
CPC ..... *G01N 21/53* (2013.01); *G01N 2015/1006* (2013.01); *G01N 2015/1452* (2013.01); *G01N 2201/0612* (2013.01)

(56) References Cited

U.S. PATENT DOCUMENTS

| | | | |
|---|---|---|---|
| 8,873,041 B1* | 10/2014 | Chai | G01N 21/65 356/301 |
| 9,952,136 B2* | 4/2018 | Javadi | G01N 15/1425 |
| 2004/0166588 A1* | 8/2004 | Farquharson | B01L 3/5023 436/169 |
| 2008/0252887 A1* | 10/2008 | Honguh | G01N 15/1434 356/338 |
| 2010/0297759 A1 | 11/2010 | Kanda | |
| 2013/0037726 A1* | 2/2013 | Kiesel | G01J 3/36 250/458.1 |
| 2014/0093949 A1* | 4/2014 | Norton | G01N 15/1459 435/288.7 |
| 2014/0200164 A1* | 7/2014 | Makarewicz, Jr. | B01F 13/0062 506/12 |
| 2015/0131099 A1* | 5/2015 | Tahara | G01N 15/1427 356/442 |
| 2015/0377764 A1* | 12/2015 | Pan | G01N 15/1434 356/36 |
| 2016/0178439 A1 | 6/2016 | Freudiger et al. | |
| 2017/0314383 A1* | 11/2017 | Ispirescu | G01N 21/65 |
| 2018/0088113 A1* | 3/2018 | Boss | G01N 33/56911 |

OTHER PUBLICATIONS

Anonymous, "Monochromatisches Licht", Wikipedia, Jan. 24, 2018, XP055457391, URL: https://de.wikipedia.org/wiki/Monochromatisches_Licht, 4 pages.

* cited by examiner

OPTICAL SYSTEM AND METHOD FOR SPECTROSCOPY

CROSS-REFERENCE TO RELATED APPLICATIONS

This application claims the benefit of and priority to German Patent Application No. 10 2016 118 898.0, filed on Oct. 5, 2016, which is hereby incorporated by reference in its entirety.

TECHNICAL BACKGROUND OF THE INVENTION

The invention relates to an optical system and a method for spectroscopy. More particularly, the present invention relates to an optical system and a method for Raman spectroscopy.

Due to its suitability for in-situ (on site) and online analysis, the Raman spectroscopy is increasingly used in industrial process and environmental measurement technology. A disadvantage in this case, however, is that some samples provide spectra, in practice due to fluorescence and/or due to their scattering properties, whose quality is impaired by a high-energy subsurface, in particular when worked with measuring times with less than 1 s, without sample preparation and/or with small-sized apparatuses.

Typically, stationary samples are used for recording Raman spectra, in which the Raman radiation generated can be integrated over a sufficiently long measuring period for the suppression of a measuring subsurface. In this case, excitation radiation of a fixed excitation wavelength is coupled into a sample to be examined and is inelastically scattered by the sample. The scattered excitation radiation can then be collected by a suitable spectroscopy arrangement and spectrally examined. Depending on the specific material properties of a sample, individual Raman lines show in the recorded spectrum which have a precisely determined spectral distance from the excitation wavelength of the excitation radiation, which is characteristic for the type of the sample.

However, such a setup is usually not suitable for recording a Raman spectrum of a moving sample because, in this case, both the excitation of the sample and the detection of an excitation radiation scattered thereon must be directed after the current position of the sample. A continuous recording of a complete Raman spectrum by a conventional spectrometer is often difficult to realize because of the integration and measurement times which are typically in the range of several tens of seconds. In particular, the measured signal intensities can be subject to considerable fluctuations due to a movement of the sample, so that generally no valid statements about the intensities of individual Raman lines with respect to one another can be obtained.

If, on the other hand, the samples to be examined are moved separately and along a fixed measuring distance, the requirements for a spectroscopic setup can be considerably reduced. For example, in the flow cytometry, individual sample elements (for example, particles, cells, viruses, microspheres) can be specifically excited and examined for their specific property. However, so far primarily fluorescence examinations have been carried out, since in a conventional flow cytometry the recording of a Raman spectrum is usually not possible due to a relatively short observation time per sample element.

It is therefore an object of the present invention to provide an optical system and a method for spectroscopy, in particular for Raman spectroscopy, with which also individual moving sample elements can be examined spectroscopically, which are not based on the complex spectroscopy setup known from the prior art, and which can be implemented with low-priced components and which are suitable for the setup of particularly small, compact and robust arrangements.

SUMMARY OF THE INVENTION

These objects are achieved according to the invention by the independent patent claims. Preferred embodiments of the invention are contained in the subclaims.

The optical system according to the invention comprises a multispectral excitation source, designed to emit monochromatic excitation radiation successively at at least two different excitation wavelengths along a common beam axis; an elongated flow volume with a longitudinal axis designed to direct a particle flow along the longitudinal axis; an excitation beam path designed to irradiate the monochromatic excitation radiation into the flow volume at a first position and a second position, wherein the first position and the second position are located in the flow volume (or laterally of the flow volume) and the first position is spaced apart from the second position; and a detection device designed to wavelength-selectively filter and detect at least one portion of a radiation scattered from the first position at a first filter wavelength and to wavelength-selectively filter and detect at least one portion of a radiation scattered from the second position at a second filter wavelength.

As a multispectral excitation source, a radiation source is applied, which is suitable for spectroscopic examinations at different excitation wavelengths. In particular, such an excitation source is characterized in that the different excitation wavelengths are essentially emitted as monochromatic excitation radiation. Preferably, it is possible to switch between the individual excitation wavelengths of the excitation source. The multispectral excitation source can be, for example, a correspondingly configured diode laser-based light source, a laser diode or a complex laser system. It is characteristic that the multispectral excitation source emits the different excitation wavelengths along a common beam axis.

Excitation radiation is particularly described as a monochromatic electromagnetic radiation, of small spectral width at a specific central wavelength (preferably in the visible (VIS), ultraviolet (UV) or infrared (IR) spectral range) as excitation wavelengths. Such excitation radiation may typically be emitted from diode lasers or laser diodes in single-mode operation. Particular preference is given to a central wavelength of 785 nm with spectral widths (FWHM) of less than 1 nm. The generation of the different excitation wavelengths can take place, for example, by using a plurality of laser diodes at different emission wavelengths as excitation wavelengths. Furthermore, the different excitation wavelengths can also be generated by a single laser diode which can be changed in its emission wavelength or a correspondingly spectrally variable diode laser. In addition to the discontinuous setting of individual wavelengths spaced apart from one another (for example, at a distance of 1 nm, 2 nm or 5 nm), a continuous tuning of individual excitation wavelengths over a specific excitation wavelength range (for example, over 5 nm, 10 nm, 15 nm or 20 nm)) can take place respectively.

In the case of the elongated flow volume with a longitudinal axis, this can be, in particular, a range adapted for a conventional flow cytometry. The flow volume may preferably comprise a microchannel or a flow cuvette which are designed to direct individual particles or sample elements through a spectroscopic interaction range by a transport stream within a transport medium. However, a flow volume according to the invention can also be formed without the presence of such a predefined guide. The flow volume can, for example, also be generated by a free enveloping flow which is designed to direct a particle stream along the longitudinal axis of the flow volume defined by it. The enveloping flow can in particular be a free flow of air or liquid. Likewise possible is the formation of a flow volume through the use of a correspondingly directed energy flow (e.g. optical transport by radiation field gradients), a potential-driven flow transport (e.g. transport of charged sample elements by an electric field) as well as other directed transport processes which enable the generation of a particle flows directed along the longitudinal axis of the flow volume. A particle flow directed in the flow volume can be defined both via the individual particles of the enveloping flow itself and via the sample elements transported through the enveloping flow.

The flow volume is therefore referred to as the volume range, within which a directed transport of sample elements (for example via a transport stream) can take place along a longitudinal axis. In particular, this is the volume range within which an interaction according to the invention of the excitation radiation with transported sample elements can take place along the longitudinal axis (interaction range). A typical example of an else directed transport process of sample elements is a transport of macroscopic sample bodies by a conveyor belt by a flow volume designed to interact with an excitation radiation according to the invention.

The flow volume is preferably at least section-wise formed tubular or as a cylindrical range. Furthermore, the flow volume may comprise tapered or widening sections. The longitudinal axis of the elongated flow volume can be curved in a straight line or arbitrarily in space. In particular, the longitudinal axis can be circular, meandering or spiral. An example of a circularly formed longitudinal axis of an elongated flow volume is the flow volume of an in-itself-circulating transport stream or a flow volume indicating a circular movement of individual particles or sample elements (e.g. annular stream of charged particles, the sample elements in a rotating reactor, circulation of liquid media).

Preferably, the transport stream and/or the individual particles or sample elements move at a common velocity through the flow volume according to the invention. The common velocity may be variable in time. It is particularly preferred that the local velocity of the transport stream and/or of the individual particles or the sample elements depend on the position along the longitudinal axis of the flow volume. In particular, this can be an accelerated or other movement (e.g., decelerated or pulsating movement) which is variable in time and location (i.e. along the longitudinal axis). Preferably, the velocity of the individual particles or sample elements is arranged such that an interaction time of the particles or sample elements with the excitation radiation at the individual positions is less than 100 ms, preferably less than 10 ms, more preferably less than 1 ms, and more preferably less than 0.1 ms. The interaction time is determined by the effective duration of the interaction between the sample elements and the excitation radiation at the individual positions. Generally, this depends on the volume of the sample elements, the effective spatial extent of the excitation radiation at the individual positions as well as on the effective velocity within the effective spatial extent of the excitation radiation at the individual positions.

The trajectories of the particles or sample elements directed along the longitudinal axis of the elongated flow volume through the spectroscopic interaction range can lie parallel to this longitudinal axis. A transport along the longitudinal axis, i.e. essentially directed transport in the direction of the longitudinal axis, however, is also present when individual particles or sample elements only move along the longitudinal axis of the elongated flow volume on a temporal average. During the transport along the longitudinal axis of the flow volume, the probe elements can in particular also perform a dither movement (e.g., by turbulence disturbances in the enveloping flow or by the Brownian motion), which is transversely directed to the longitudinal axis additional.

The excitation beam path is a part of the optical system according to the invention, through which the monochromatic excitation radiation of the excitation source is irradiated into the flow volume. If, in particular, a sample element is located within the flow volume, interaction with the sample element can occur. In this case, the excitation radiation is preferably irradiated several times at different positions along the longitudinal axis of the flow volume into the flow volume. In particular, at at least one first position and at one second position it will be irradiated into the flow volume, wherein the first position and the second position are located in the flow volume and the first position being spaced apart from the second position. The excitation beam path comprises all optical components which serve to irradiate the excitation radiation into the flow volume, in particular to irradiate a sample element that flows through the flow volume.

The detection device is intended to wavelength-selectively filter and detect, at least at a first filter wavelength and one second filter wavelength, at least a portion of the excitation radiation scattered within the flow volume, in particular the excitation radiation scattered by the sample element during the irradiation of a sample element flowing through the flow volume. In particular, a detection and filtering is carried out of radiation scattered at the first position and at the second position along the longitudinal axis of the flow volume. The detection device comprises all optical components which serve to filter and detect at least a portion of the excitation radiation scattered within the flow volume.

The idea of the present invention is that a directed particle flow or transport stream allows a multiple interaction of excitation radiation with the flow volume, through an essentially one-dimensional orientation along the longitudinal axis of a flow volume, and thereby provides a simplified way for multiple examinations even with moving sample elements. In particular, when irradiating a monochromatic excitation radiation of a fixed excitation wavelength at more than one position, the effective measurement and observation time can be extended. The recording of a Raman spectrum is made possible by the fact that the necessary measurement and integration times for recording a spectrum can be considerably reduced by the irradiation of monochromatic excitation radiation at several different excitation wavelengths at different irradiation positions by subsequent Raman-selective filtering and detection of the generated scattered radiation. In particular, if the position of a moving sample element is correlated with an alternation between the different excitation wavelengths of the excitation source, a very fast recording of spectra can be carried out without the need for complex spectroscopy setups. It is possible to work with low-priced components and the setup of particularly small, compact and robust arrangements is made possible.

Preferably, the excitation source is a narrow-band laser diode which can be tuned spectrally over a wide range and is directly frequency-modulated. Here, narrow-banded relates to laser diodes, its emitted radiation is limited to a very narrow spectral range. This is particularly the case, if it is about laser diodes in single-mode operation. In this case, line widths below 1 nm (FWHM) are typically achieved. Particularly preferred line widths (FWHM) are below 10 nm, below 5 nm, below 1 nm, and below 0.1 nm. Depending on the wavelength range, this corresponds to frequency bandwidths in the lower THz range down to the MHz range. For excitation, preferably, excitation radiation is suitable for excitation wavelengths in the range of about 785 nm, furthermore excitation wavelengths of the entire near-infrared spectral range, the visible spectral range as well as the ultraviolet, infrared and the far-infrared spectral range.

Furthermore, it is preferred that the laser diodes are spectrally tunable over a wide spectral range. This has the advantage that an excitation source can provide a wide spectrum of possible excitation wavelengths. Likewise preferred are laser diodes, in which different modes can be excited, so that, for example, also larger, at least discretely, at a distance of several 10 nm, wavelengths which can be achieved. Directly frequency-modulated laser diodes, in which a wavelength change can be adjusted by intrinsic diode parameters, for example via a temperature or a current, are also preferred. Preferably, so-called two-wavelength laser lasers can be used, for example a Y-branched two-wavelength DBR diode laser (also referred to as a Y-branch DBR-RW diode laser) [Maiwald et al., "Dual-Wavelength Y-Branch Distributed Bragg Reflector Diode Laser at 785 Nanometers for Shifted Excitation Raman Difference Spectroscopy;" Appl. Spectrosc. 69, 1144-1151 (2015)]. Furthermore, it is also preferred that the excitation source is a correspondingly narrow-band diode laser which can be tuned spectrally over a wide range. This may be, for example, an ECDL system or a spectrally tunable diode-pumped solid-state laser. Furthermore, for example, correspondingly tunable dye or fiber lasers or the individual "prongs" (spectral lines) of an optical frequency comb are suitable.

Preferably, the filter elements are narrow-band passive bandpass filters, wherein a filter wavelength is determined by the central wavelength of such a bandpass. These may in particular be dichroic filters, Bragg filters or Fabry-Pérot filters. It is also possible to use a diffractive grating, an etalon or a Mach-Zehnder interferometer. As wavelength-selective in this case is in particular understood, a filter in which the filter wavelength is transmitted by the filter element with a maximum intensity and the spectral ranges adjacent to the filter wavelength are suppressed or blocked. The filter wavelength is the central wavelength of the passband (also referred to as a transmission band or passband) of the filter element. In the case of symmetrical bandpasses, this results from the spectral position of the bandpass center. Passive means that no active change of the filter properties of the filter element takes place for recording a Raman spectrum, but in particular that the respective filter wavelengths of a filter element are time-invariant. Narrow-band means that the spectral width of the bandpass refers to a limited spectral range. Particularly preferred passband widths (FWHM) are here below 10 nm, below 5 nm, below 1 nm, and below 0.1 nm. Depending on the wavelength range, this corresponds to frequency bandwidths in the lower THz range down to the MHz range. A narrow-band-transmitting bandpass filter is thus to be understood as a filter element which has essentially a high transmission for incident radiation with identical wavelength at the respective filter wavelength (central wavelength of the passband), but suppresses a transmission for radiation in a range directly adjacent to the respective filter wavelength. Here, "directly" is defined over the filter bandwidth of the respective passband.

Preferably, the transmitted filter wavelengths of the individual filter elements differ both from one another and also from the individual excitation wavelengths of the excitation radiation. This means that, in the detection device, preferably inelastic scattered excitation radiation can be detected, since the filter wavelengths transmitted through the individual filter elements differ from the individual excitation wavelengths of the excitation radiation.

For recording a (discrete) Raman spectrum (i.e. the spectral progression of Raman signals), it is particularly preferred if the spectral distance between at least one excitation wavelength of the excitation source and a filter wavelength of a filter element corresponds to a Raman shift of the excitation radiation scattered by a sample element. For this purpose, the transmitted filter wavelengths of the individual filter elements are preferably detected by an individually assignable detector, and at least one first intensity and one second intensity are determined for each excitation wavelength. An individually assignable detector can, for example, also be an individually assigned detection range of a line detector or a single or single-channel detector whose detection signal can be assigned unambiguously to a transmitted filter wavelength of the individual filter elements. Such an assignment can also take place by a temporal separation of the detection signals. The intensities determined by the detection device can be evaluated by a suitable means for determining a Raman spectrum in such a way that a Raman spectrum is determined from at least two determined intensities. The number of excitation wavelengths used in the spectral evaluation gives the density of the resolvable (discrete) spectral lines.

Preferably, the detectors used are single-channel detectors. These can be arranged as individual single-channel detectors or multi-channel detectors which can be individually read out as corresponding to single-channel detectors. This has the advantage that particularly inexpensive, compact and robust detector devices can be used. The use of a high-resolution, particularly low-noise and sensitive CCD camera is not required. If multi-channel detectors are operated via single channels as individual single-channel detectors, then a plurality of channels can also be combined to form a single-channel detector. An independent reading of the individual channel bundles should be possible.

Preferably, the excitation beam path is designed to irradiate into the flow volume at least at a first position with the excitation radiation at a first excitation wavelength and to irradiate into the flow volume at least at a second position with the excitation radiation at a second excitation wavelength. This embodiment of the invention corresponds to an arrangement in which excitation radiation of the excitation source is successively irradiated into the flow volume at different excitation wavelengths at different positions along the flow volume. In an alternative embodiment of the invention, excitation radiation of the excitation source of a first excitation wavelength can be irradiated into the flow volume at at least two different positions along the flow volume, and excitation radiation of the excitation source of a second excitation wavelength can be irradiated into the flow volume at least one further position which is different from the first two positions. Such an arrangement can, for example, be used to confirm a measurement result determined at a position at a first excitation wavelength, or to increase the available measurement time for a measurement at an excitation wavelength. Furthermore, such an arrangement can be used for SERDS (Shifted Excitation Raman Difference Spectroscopy). The determination of a difference spectrum makes it possible, in contrast to the mere evaluation of recorded single-spectra, to draw more precise conclusions about a Raman sample. In particular, influences of the measuring background can be effectively filtered out. Since according to the invention, however, a determination of single Raman spectra is not carried out by a spectrometer, but by irradiating a sample element with excitation radiation of different excitation wavelengths, this method is also referred to as TERDS (Tunable Excitation Raman Difference Spectroscopy).

Preferably, the optical system comprises a collecting optical system designed to collect a radiation which is essentially scattered from a first position and to collect a radiation which is essentially scattered from a second position, and to direct the collected radiation onto the detection device. In particular, the collecting system can comprise a positionally variable objective lens which is designed to change in its position in accordance with a particle flow flowing through the flow volume along its longitudinal direction in such a way that the velocity of the objective lens essentially correlates with the flow velocity of the flowing particle flow or is at least is adapted thereto. Preferably, a sample element is transported along the longitudinal axis of the flow volume through the flow volume, wherein the positionally variable objective lens adapts its position to the position of the sample element. In a further preferred embodiment of the invention, the collecting system according to the invention comprises a cylindrical lens whose longitudinal axis is essentially aligned in the direction of the longitudinal axis of the flow volume. As a result, radiation scattered out of the flow volume can be collected along the entire longitudinal axis of the flow volume and directed onto the detection device. In a likewise preferred embodiment of a collecting system according to the invention, this comprises a plurality of individual lenses or individual objectives, which are essentially aligned along the direction of the longitudinal axis of the flow volume. This at least allows a collection of radiation scattered out of the flow volume along discrete positions along the longitudinal axis of the flow volume. Particularly preferably, the positions of the individual single lenses or individual objectives correlate with the irradiation positions of the excitation radiation along the longitudinal axis of the flow volume. The optical system according to the invention can also comprise a plurality of different collecting optical systems (for example, positionally variable objective lens and cylindrical lens along individual sections of the flow volume, or collecting devices for different collection directions), wherein similar collecting systems can be combined into a common collecting system.

Preferably, the optical system according to the invention further comprises a means for determining the position, which is designed to determine the position of a sample element flowing along the longitudinal axis of the flow volume. The sample element is preferably a single cell or a particle which can be excited by a corresponding excitation radiation for scattering and/or fluorescence. In particular, the sample element is preferably a sample which can be excited to inelastic scattering. Preferably, a Raman spectrum can be determined from the sample element. The means for determining the position can preferably be a means for determining the optical position (for example, by machine vision).

Preferably, the optical system according to the invention further comprises a means for switching, which is designed to switch between at least two excitation wavelengths of the excitation source in dependence on the position of a sample element along the longitudinal axis of the cylindrical flow volume. Preferably, switching between a first excitation wavelength of the excitation source and a second excitation wavelength of the excitation source occurs when the sample element is located in the range between a first position and a second position along the longitudinal axis of the flow volume. It is also preferred that switching between individual excitation wavelengths of the excitation source takes place only when the sample element is located in the range between the individual positions along the longitudinal axis of the flow volume.

Preferably, the detection device of the optical system according to the invention comprises at least one beam splitter at which the radiation collected by the collection system is divided into at least two beam paths, wherein a wavelength-selective filtering in a first beam path by a first filter element at a filter wavelength is performed and a wavelength-selective filtering in a second beam path by a second filter element at a second filter wavelength is performed. The detection device according to the invention can comprise further beam splitters for dividing the radiation collected by the collecting optical system into a plurality of different beam paths. Different filter elements with different filter wavelengths can be assigned to the individual beam paths of the detection device. Each beam path can comprise an exclusively reserved detector for this beam path.

A further aspect of this invention relates to a method for spectroscopy, in particular for Raman spectroscopy, on individual sample elements. An optical system for spectroscopy according to the invention can preferably be provided for carrying out the method. The method for spectroscopy comprises a flow transport of a sample element along a longitudinal axis of an elongated flow volume from a first end of the flow volume to a second end of the flow volume; irradiating the sample element with monochromatic excitation radiation of a first excitation wavelength of an excitation source at a first position along the longitudinal axis of the flow volume; switching from the first excitation wavelength of the excitation source to a second excitation wavelength of the excitation source, if the sample element is located in the range between the first position and a second position along the longitudinal axis of the flow volume; irradiating the sample element with monochromatic excitation radiation of the second excitation wavelength of the excitation source at a second position along the longitudinal axis of the flow volume.

The sample elements can be, in particular, cells, molecules or other micro- or nano-particles. Furthermore, the sample elements can be macroscopic bodies or objects suitable for Raman spectroscopy. The sample elements can be examined individually (single mode) or in conjunction (bulk mode). Furthermore, the sample elements can be distributed homogeneously or approximately homogeneously (the same or approximately the same sample element density) along the flow volume. In particular, the individual sample elements can also completely fill the flow volume. Explanations for the individual features of the method according to the invention can be found in the corresponding descriptions of the optical system according to the invention. All explanations given for the individual embodiments of the optical system according to the invention apply correspondingly.

Preferably, the method according to the invention further comprises a wavelength-selective filtering of the excitation radiation, scattered by the sample element, of a first excitation wavelength of the excitation source by a first filter element and at least one second filter element, wherein a first transmitted filter wavelength of the first filter element and a second transmitted filter wavelength of the second filter element differ from the first excitation wavelength; and a wavelength-selective filtering of the excitation radiation, scattered by the sample element, of a second excitation wavelength of the excitation source by a first filter element and at least one second filter element, wherein a first transmitted filter wavelength of the first filter element and a second transmitted filter wavelength of the second filter element differ from the second excitation wavelength.

BRIEF DESCRIPTION OF THE FIGURES

The invention is explained below in exemplary embodiments with reference to the accompanying drawings. In particular.

DETAILED DESCRIPTION OF THE INVENTION

Figure 1A:
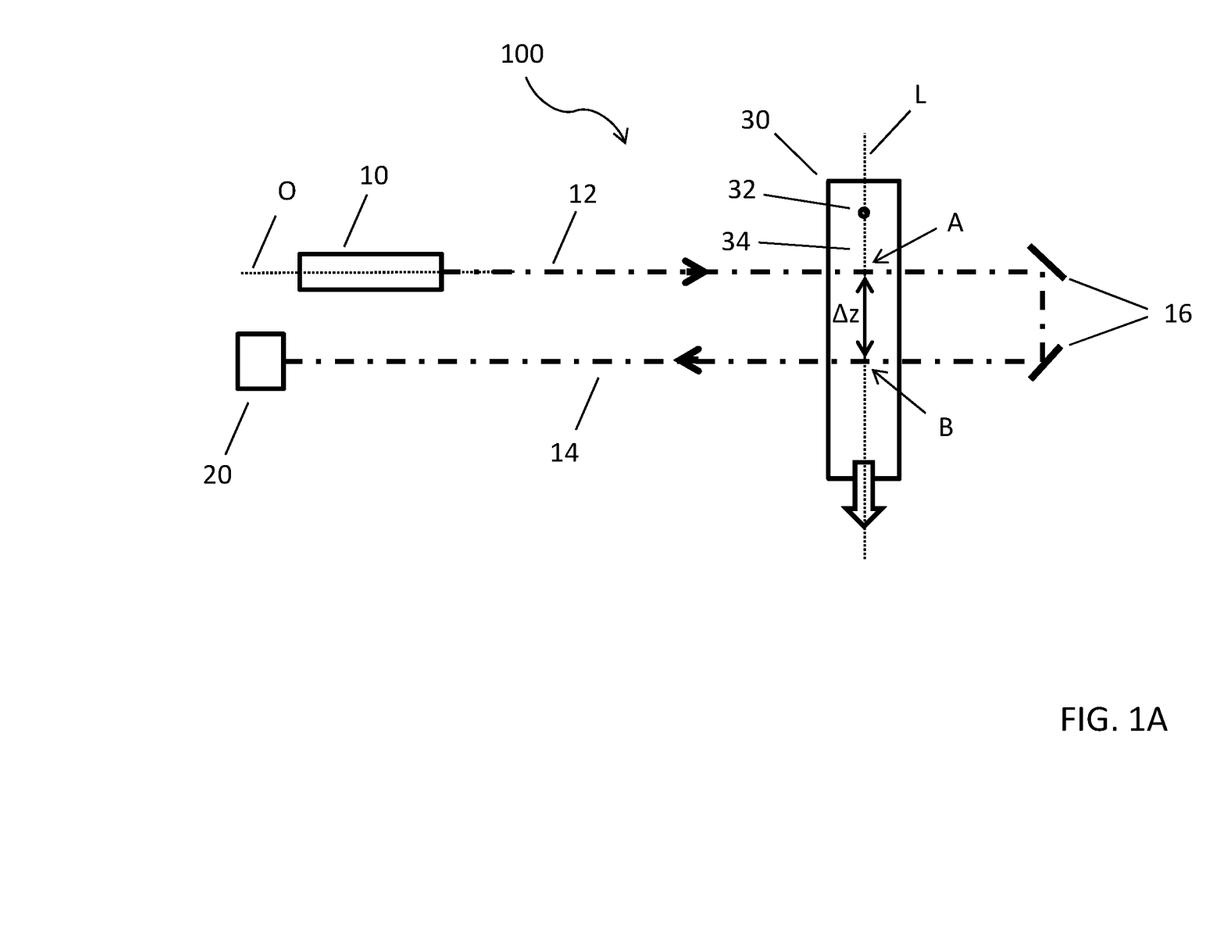
FIGS. 1A-1C show schematic representations of a first embodiment of an optical system for spectroscopy according to the invention in side view.
Figure 1B:
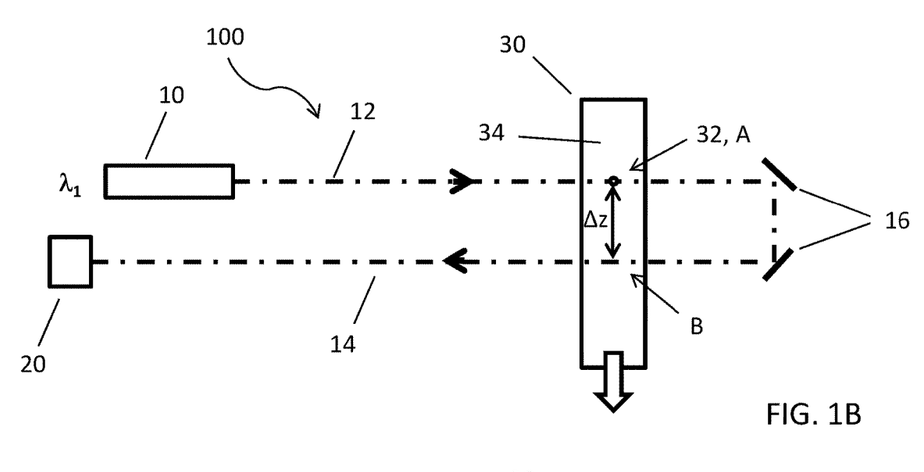
Figure 1C:
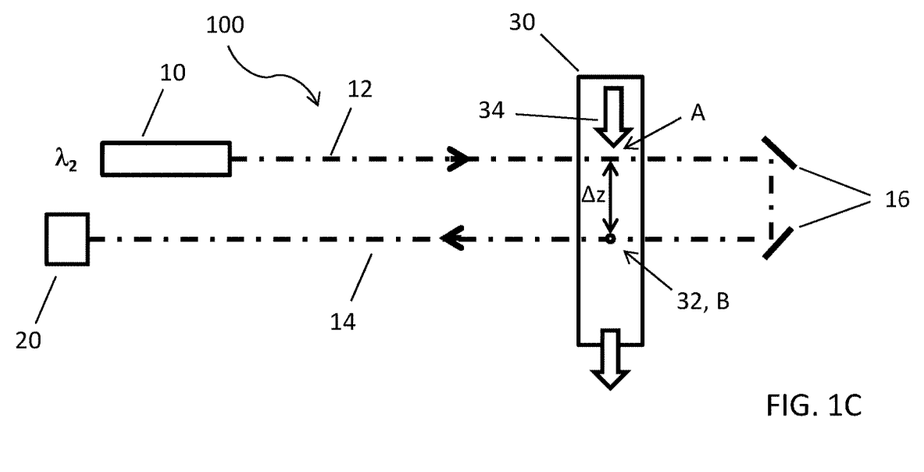

FIGS. 1A to 1C show schematic representations of a first embodiment of an optical system 100 for spectroscopy according to the invention in side view. A multispectral excitation source 10 can emit monochromatic excitation radiation 12, 14 at at least two different excitation wavelengths $\lambda_1$, $\lambda_2$ along a common beam axis O. The excitation radiation 12, 14 emitted by the excitation source 10 is irradiated several times into an elongated extended flow volume 30 with a longitudinal axis L. In particular, in this embodiment, the excitation radiation 12 emitted along the beam axis O in a first direction is deflected after a first passage through the flow volume 30, by a correspondingly arranged deflecting mirror 16 or another deflection device designed for beam deflection, in such a way that the excitation radiation 14 propagating thereafter in a second direction can also pass through the flow volume 30. The excitation radiation therefore enables a multiple passing through of the excitation radiation 12, 14 through the flow volume 30. In this case, the monochromatic excitation radiation 12, 14 is irradiated at a first position A and a second position B into the flow volume 30, wherein the first position A and the second position B are located in the flow volume 30 and the first position A is spaced apart from the second position B by $\Delta z$. After passing twice through the flow volume 30, the excitation radiation 14 propagating in the second direction is blocked at a beam dump 20. However, the precise arrangement of the beam path or of the individual components of the beam path can, in principle, be selected freely, in particular additional deflection devices can be intended outside the flow volume 30 for further deflection of the excitation radiation.

The embodiment shown FIG. 1A to 1C is characterized in that the excitation radiation 12, 14 is irradiated from different directions into the flow volume 30, resulting in a continuous uniaxial beam path between the excitation source 10 and the beam dump 20. In particular, in this embodiment, irradiation of excitation radiation 12, 14 into the flow volume 30 takes place from two mutually opposite directions. In general, these directions can also be arranged tilted and have corresponding angles to one another. Parallelism of the individual directions is not necessary.

The flow volume 30 can be, for example, the analysis area of a flow cuvette. The lateral limitation of the flow volume 30 as well as the longitudinal axis L are predetermined by the shaping of the cuvette channel. Within the flow volume 30, a flow can be generated which is suitable for directing a particle flow along the longitudinal axis L. In particular, this can be a flowing solvent or dispersant as carrier medium for a sample element 32. A sample element 32 can preferably be transported by flow transport along the longitudinal axis L of the flow volume 30 from a first end of the flow volume 30 to a second end of the flow volume 30. In particular, the sample elements 32 can be individual cells.

FIG. 1A shows the schematic representation at a point in time at which a sample element 32 transported along the longitudinal axis L of the flow volume 30 in the direction of position A is located above the positions A and B at which a position-dependent irradiation of excitation radiation 12, 14, into the flow volume 30 can take place. FIG. 1B shows the same schematic representation at a later point in time at which the sample element 32 has moved to the position A by the flow transport. According to the invention, an irradiation of the sample element 32 with monochromatic excitation radiation 12, 14 of a first excitation wavelength $\lambda_1$ of the excitation source 10 can take place at the position A. FIG. 1C shows the schematic representation at a even later point in time at which the sample element 32 was transported further from the position A to the position B. According to the invention, an irradiation of the sample element 32 with monochromatic excitation radiation 12, 14 of a second excitation wavelength $\lambda_2$ of the excitation source 10 can take place at the position B. A switching from the first excitation wavelength $\lambda_1$ of the excitation source 10 to the second excitation wavelength $\lambda_2$ of the excitation source 10 preferably takes place when the sample element 32 is located in the range between the first position A and the second position B along the longitudinal axis L of the flow volume 30. For this purpose, the position of a flowing sample element 32 along the longitudinal axis L of the flow volume 30 can be determined.

Figure 2:
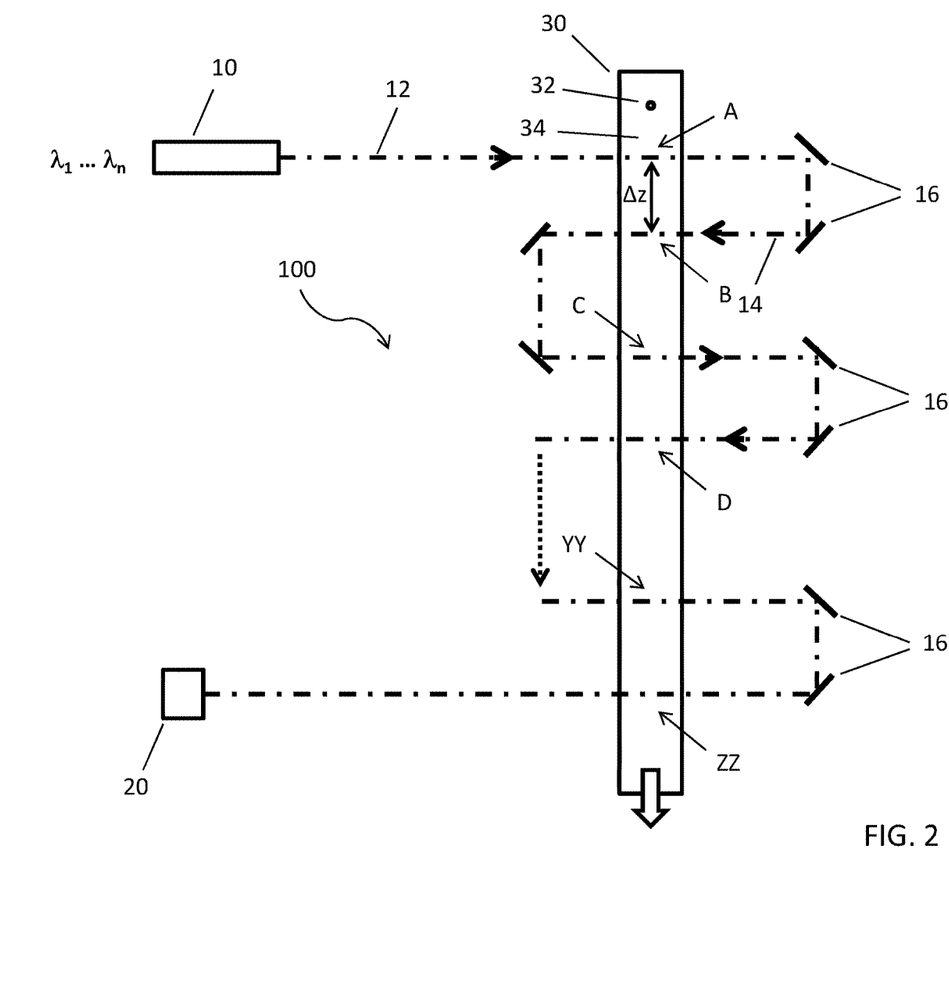
FIG. 2 shows a schematic representation of an extended variant of the optical system for spectroscopy according to the invention, shown in FIGS. 1A-1C, in side view.

FIG. 2 shows a schematic representation of an extended variant of the optical system 100 for spectroscopy according to the invention, shown in FIGS. 1A-1C, in side view. The reference signs used in FIG. 2 correspond to the reference signs used in FIGS. 1A to 1C. The explanation for the individual reference signs given in the accompanying descriptions of figures apply correspondingly. The embodiment was extended in that the excitation radiation 12, 14 can be irradiated into the flow volume 30 at further positions C, D, . . . by arranging further deflecting mirrors 16 (or other suitable deflection devices). For this purpose, the excitation beam path has several successive alternating sections with excitation radiation 12 running in a first direction and excitation radiation 14 running in a second direction. The excitation radiation can thereby be irradiated into the flow volume 30 at a plurality of positions, i. a first position A, a second position B, a third position C, etc., coming from different directions. The total number of the irradiation positions can be selected according to the length of the longitudinal axis L of the flow volume 30. The distance $\Delta z$ between the individual irradiation positions can vary. Individual or all irradiation directions may also differ from one another.

According to the embodiments for FIGS. 1A to 1C, switching between the individual excitation wavelengths $\lambda_1 \ldots \lambda_n$ of the excitation source 10 can take place if the sample element 32 is located in the range between two adjacent positions along the longitudinal axis L of the flow volume 30. Here, it is preferred if the number of possible excitation wavelengths $\lambda_1 \ldots \lambda_n$ of the excitation source 10 corresponds to the total number of the irradiation positions. Even when the number of excitation wavelengths $\lambda_1 \ldots \lambda_n$ of the excitation source 10 is smaller than the total number of irradiation positions, it is possible to arbitrarily switch between them. In particular, switching between mutually adjacent irradiation positions is not required and a specific excitation wavelength $\lambda_1 \ldots \lambda_n$ of the excitation source 10 can be irradiated at a plurality of irradiation positions. Thus, in particular, the effective time of an interaction between the excitation radiation 12, 14 of a specific excitation wavelength $\lambda_1 \ldots \lambda_n$ and a sample element 32 can be increased. In particular, excitation can take place by a cascade of multiple alternating excitation radiation 12, 14 with specific excitation wavelengths $\lambda 1 \ldots \Lambda n$ in arbitrary permutations along the longitudinal axis L of the elongated flow volume 30. Such a multiple excitation at specific excitation wavelength $\lambda_1 \ldots \lambda_n$ can be used in particular for SERDS applications. Furthermore, the measuring accuracy of the respective Raman signals at the individual excitation wavelengths $\lambda_1 \ldots \lambda_n$ can thereby be improved by a corresponding averaging.

Figure 3A:
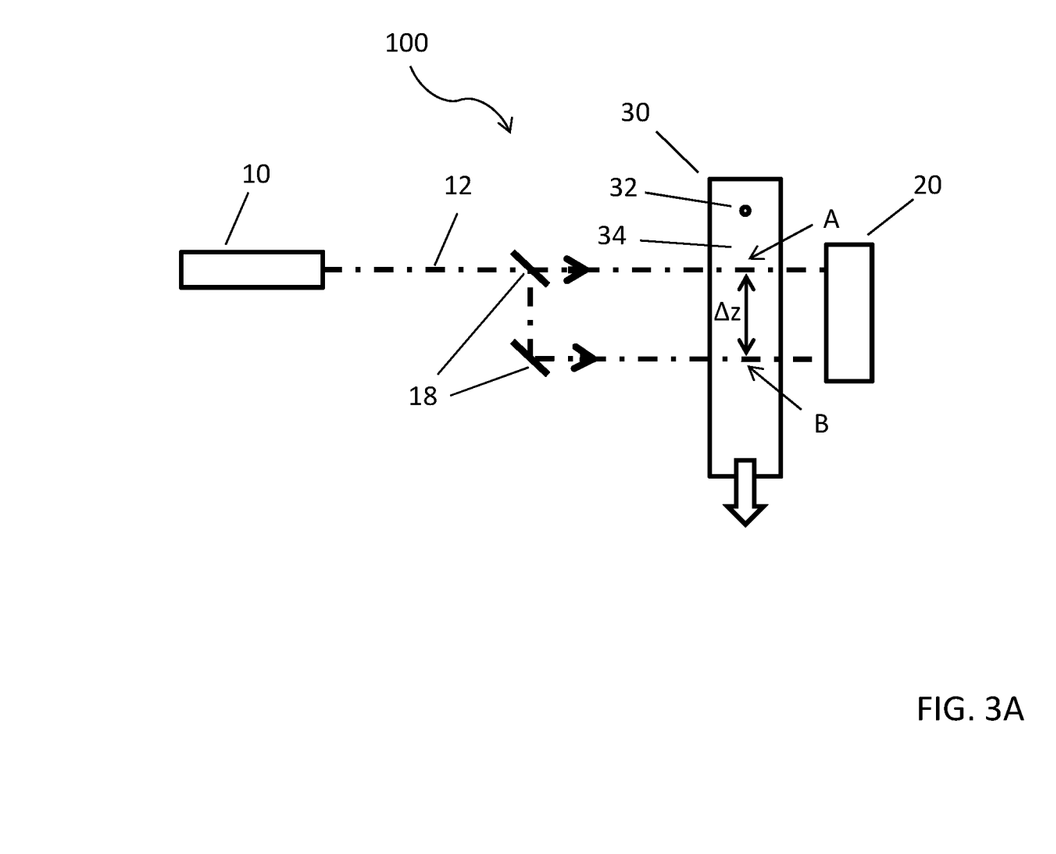
FIGS. 3A-3C show schematic representations of a first embodiment of an optical system for spectroscopy according to the invention in side view.
Figure 3B:
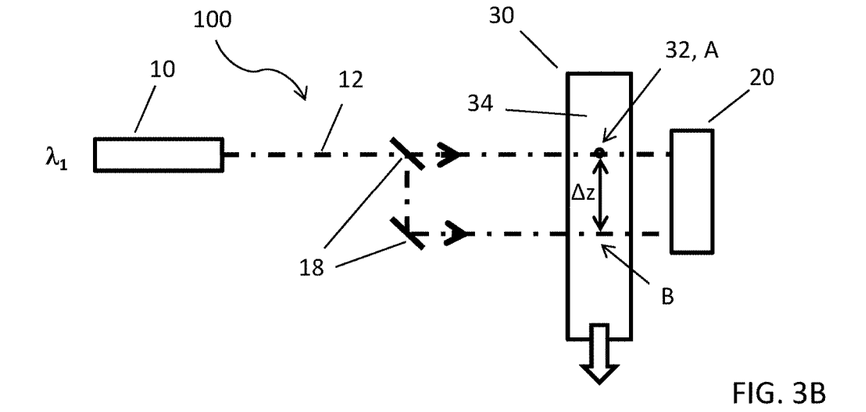
Figure 3C:
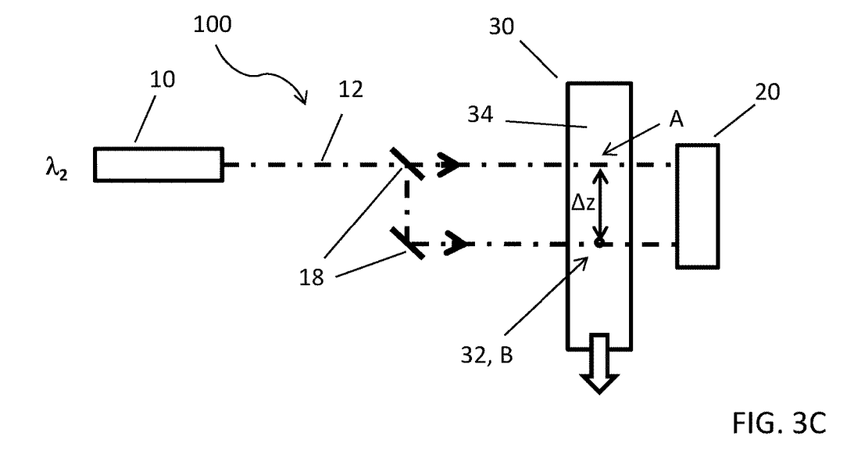

FIGS. 3A to 3C show schematic representations of a second embodiment of an optical system 100 for spectroscopy according to the invention in side view. The reference signs used in FIGS. 3A to 3C largely correspond to the reference signs used in FIGS. 1A to 1C. The explanation for the individual reference signs given in the accompanying descriptions of figures apply correspondingly. In this embodiment as well, an excitation radiation 12 of an excitation source 10 is irradiated into a flow volume 30 at a first position A and at a second position B. In contrast to the arrangement shown in FIGS. 1A to 1C, however, the beam path used for this purpose is not a single beam which is single or multiply folded by deflection, but the beam path is split in this case by the use of beam splitters 18 in such a way, that an irradiation into the flow volume 30 at the first position A and at the second position B can take place de facto simultaneously. Furthermore, in such an embodiment, the excitation radiation 12 interacts only once with the flow volume 30. This is particularly advantageous when the flow volume has only a low transmittance (high absorption or scattering) for the excitation radiation 12, for example when using a turbid medium as a enveloping flow or because of a high sample element density. For the embodiments shown in FIGS. 3A to 3C, it is characteristic that the excitation radiation 12 is in each case irradiated into the flow volume 30 from a common direction (but spaced apart), wherein the beam path is split up twice in advance (or even several times). The excitation radiation 12 is split by the beam splitters, wherein the individual partial beams of the excitation radiation 12 is irradiated into the flow volume 30 at individual irradiation positions. In particular, in the embodiment shown here, irradiation of excitation radiation 12 into the flow volume 30 takes place from two directions extending parallel to one another. In general, however, in this embodiment as well, the directions can be tilted relative to each other and have corresponding angles to each other (for example, for process monitoring within reactors). Parallelism of the individual directions is also not required. The partial beams of the excitation beam path can be blocked after irradiation into the flow volume 30 by a single or a plurality of beam dumps 20.

Moreover, said first and second embodiments can also be combined arbitrarily with one another, i.e. in a corresponding beam path, elements for deflection as well as for beam splitting can be used.

Figure 4:
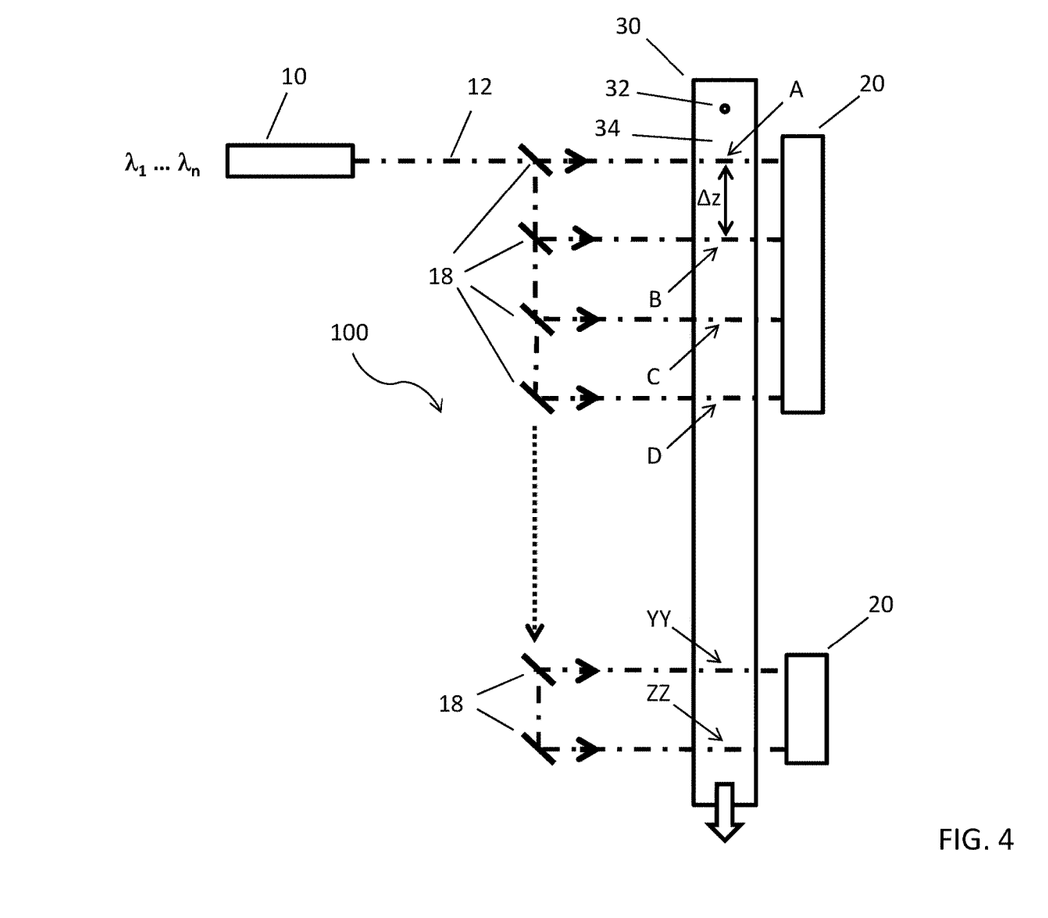
FIG. 4 shows a schematic representation of an extended variant of the embodiment of an optical system for spectroscopy according to the invention shown in FIGS. 3A-3C in a side view.

FIG. 4 shows a schematic representation of an extended variant of the embodiment of an optical system 100 for spectroscopy according to the invention shown in FIGS. 3A-3C in a side view. The reference signs used in FIG. 4 correspond to the reference signs used in FIGS. 3A to 3C. The explanation for the individual reference signs given in the accompanying descriptions of figures apply correspondingly. The embodiment is, analogous to FIG. 2, extended in that the excitation radiation 12 can be irradiated into the flow volume 30 at further positions C, D, . . . by arrangement of additional beam splitters 18. In this case, the excitation beam path has several essentially identical parallel sections. The excitation radiation 12 is thereby irradiated into the flow volume 30 at a plurality of positions, i.e. a first position A, a second position B, a third position C, etc. . . . . The total number of the irradiation positions can be chosen according to the length of the longitudinal axis L of the flow volume 30. The distance $\Delta z$ between the individual irradiation positions can vary. Also, individual or all directions can differ from each other.

According to the explanations to 1A to 1C, it is also possible that switching between individual excitation wavelengths $\lambda_1 \ldots \lambda_n$ of the excitation source 10 takes place, when the sample element 32 is located in the range between two adjacent positions along the longitudinal axis L of the flow volume 30. Here, it is preferred if the number of possible excitation wavelengths $\lambda_1 \ldots \lambda_n$ of the excitation source 10 corresponds to the total number of the irradiation positions. Even if the number of excitation wavelengths $\lambda_1 \ldots \lambda_n$ of the excitation source 10 is smaller than the total number of irradiation positions, it can be arbitrarily switched between these. In particular, switching between mutually adjacent irradiation positions is not required and a specific excitation wavelength $\lambda_1 \ldots \lambda_n$ of the excitation source 10 can be irradiated at a plurality of irradiation positions. Thus, in particular, the effective time of an interaction between the excitation radiation 12 of a specific excitation wavelength $\lambda_1 \ldots \lambda_n$ and a sample element 32 can be increased.

Figure 5:
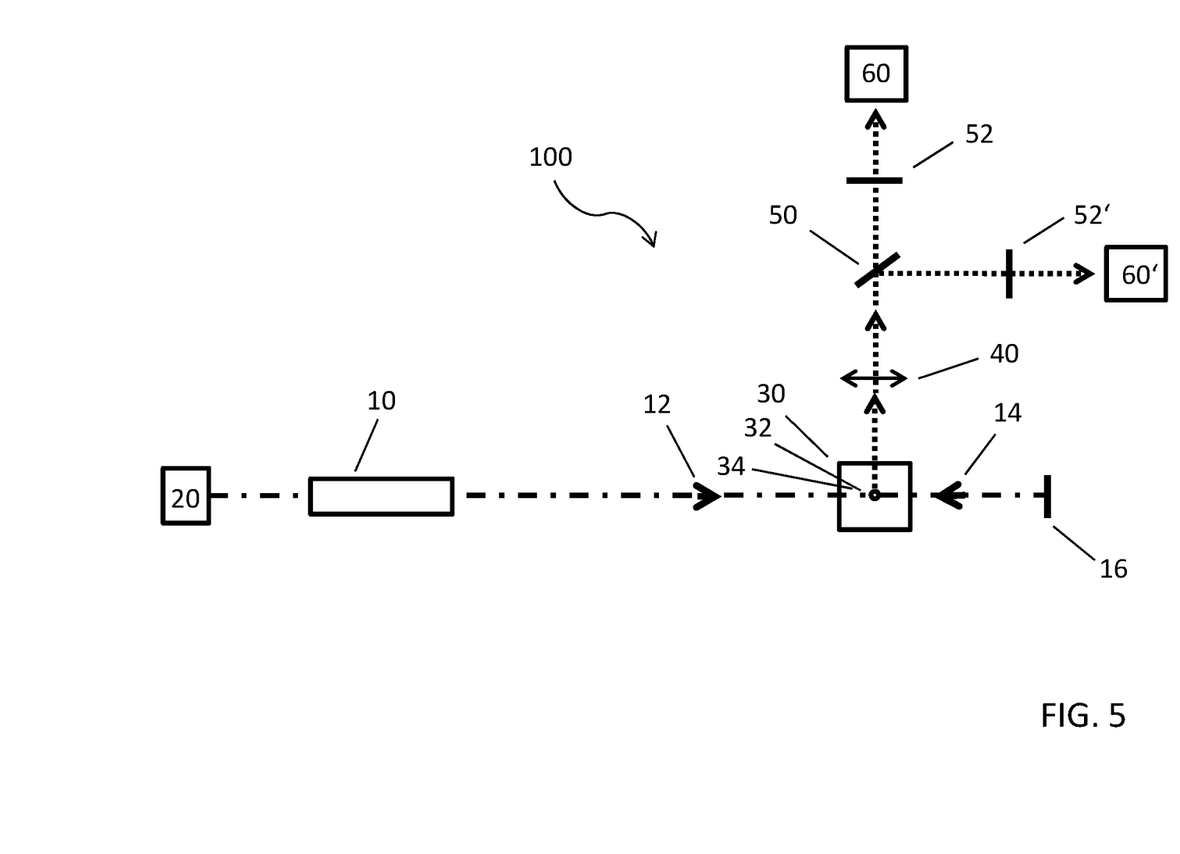
FIG. 5 shows a schematic representation of an embodiment of an optical system for spectroscopy according to the invention according to FIG. 1A-1C or 2 in plan view.

FIG. 5 shows a schematic representation of an embodiment of an optical system 100 for spectroscopy according to the invention according to FIG. 1A-1C or 2 in plan view. The reference signs used in FIG. 5 largely correspond to the reference signs used in FIGS. 1A to 1C. The explanation for the individual reference signs given in the accompanying descriptions of figures apply correspondingly. The excitation radiation 12, 14, which is scattered at the various irradiation positions, is collected by a collecting optical system 40 and directed to a detection device 50, 52, 52', 60, 60'. The task of the detection device 50, 52, 52', 60, 60' is to wavelength-selectively filter and detect at least a portion of radiation scattered at the different irradiation positions at least at a first filter wavelength $f_1$ and a second filter wavelength $f_2$. In particular, the detection device can comprise at least one beam splitter 50, at which the radiation collected by the collecting optical system 40 is divided into at least two beam paths, wherein in a first beam path, wavelength-selective filtering is performed by a first filter element 52 at a first filter wavelength $f_1$ and in a second beam path a wavelength-selective filtering is performed by a second filter element 52' at a second filter wavelength $f_2$. The radiation transmitted at the first filter wavelength $f_1$ through the first filter element 52 is subsequently detected by a first detector 60 while the radiation transmitted at the second filter wavelength $f_2$ through the second filter element 52' is detected by a second detector 60'.

Figure 6:
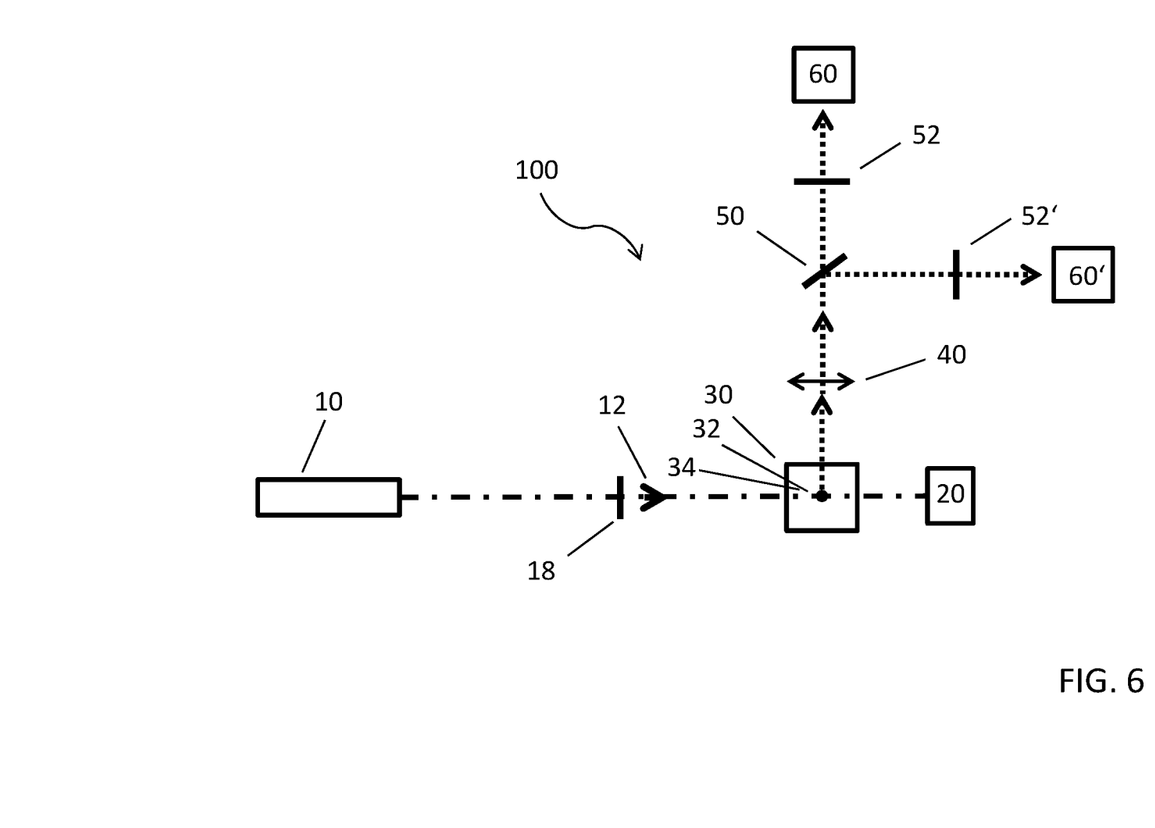
FIG. 6 shows a schematic representation of an embodiment of an optical system for spectroscopy according to the invention according to FIG. 3A-3C or 4 in plan view.

FIG. 6 shows a schematic representation of an embodiment of an optical system 100 for spectroscopy according to the invention according to FIG. 3A-3C or 4 in plan view. The reference signs used in FIG. 6 largely correspond to the reference signs used in FIG. 5. The explanation for the individual reference signs given in the accompanying descriptions of figures apply correspondingly. Deviations arise only in relation to the selected embodiment of the excitation beam path. This corresponds to the embodiment shown in FIGS. 3A to 3C or 4 and has at least one beam splitter 18 instead of a deflecting device (deflecting mirror 16) for folding the excitation beam path. Furthermore, the position of the beam dump 20 is also influenced by the changed excitation beam path.

Figure 7:
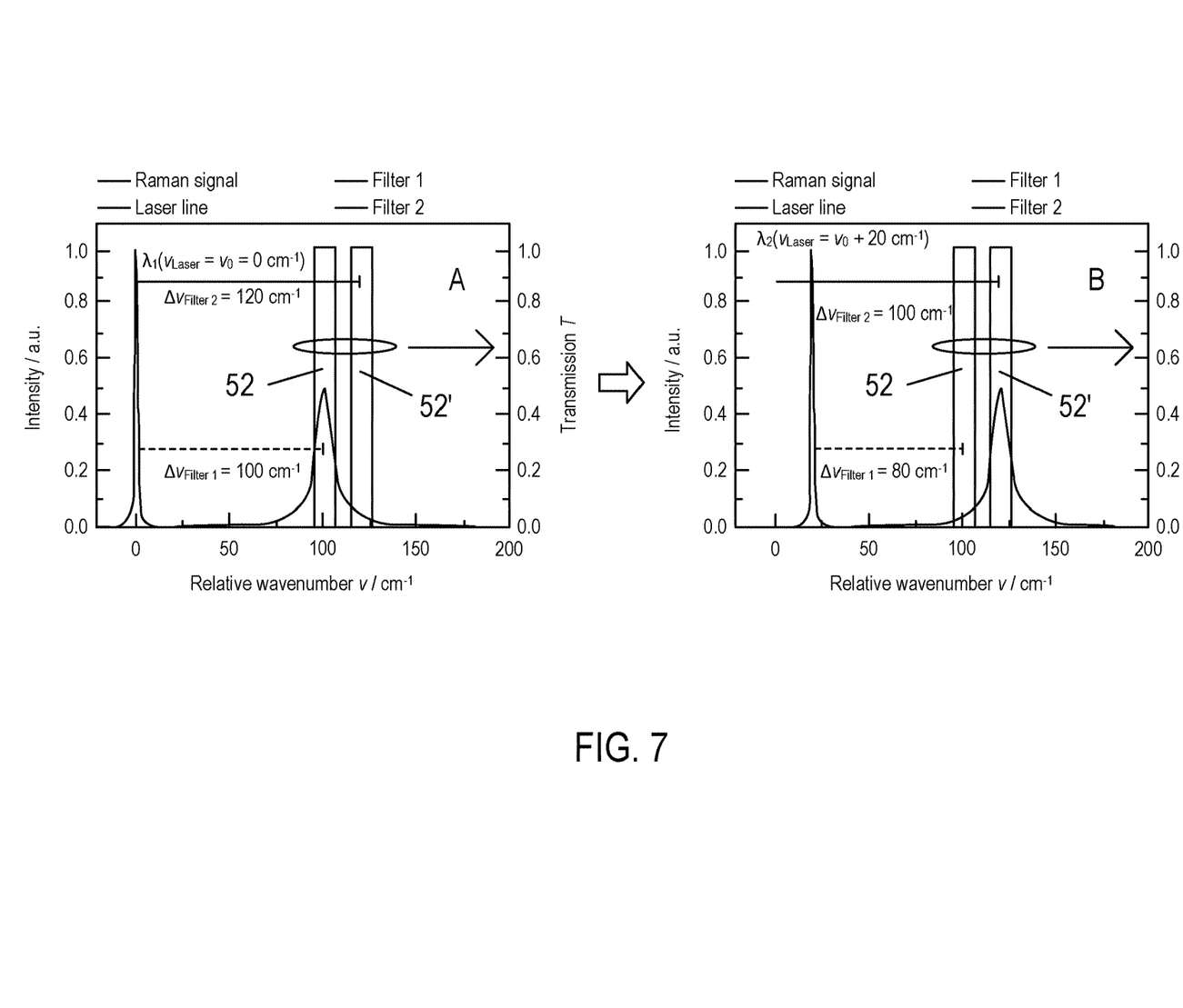
FIG. 7 shows a general scheme for recording a Raman spectrum applying a method according to the invention.

FIG. 7 shows a general scheme for recording a Raman spectrum applying a method according to the invention. By means of a wavelength-selective filtering and detection of an excitation radiation 12, 14, scattered by a sample element 32, of a first excitation wavelength $\lambda_1$ of an excitation source 10, by a first filter element 52 and at least one second filter element 52', wherein a transmitted first filter wavelength $f_1$ of the first filter element 52 and a transmitted second filter wavelength $f_2$ of the second filter element 52' differ from the first excitation wavelength $\lambda_1$ and a wavelength-selective filtering and detection of the excitation radiation 12, 14, scattered by the sample element 32, of a second excitation wavelength $\lambda_2$ of the excitation source 10 by a first filter element 52 and at least one second filter element 52', wherein a transmitted first filter wavelength $f_1$ of the first filter element 52 and a transmitted second filter wavelength $f_2$ of the second filter element 52' differ from the second excitation wavelength $\lambda_2$, on condition of that the spectral distance between at least one excitation wavelength $\lambda_1$, $\lambda_2$ of the excitation source 10 and a filter wavelength $f_1$, $f_2$ of a filter element 52, 52' corresponds precisely to a Raman shift of the excitation radiation 12, 14 scattered by the sample element 32, a discrete Raman spectrum of the sample element 32 can be determined.

In the diagrams A and B, as the abscissa, the relative wave number respectively, i.e. the wave number difference to the wave number of a specific reference wave in $cm^{-1}$, are applied. A wave of a first excitation wavelength of the excitation source is selected as the reference wave. The ordinate is the intensity of the radiation. The spectral progression of the intensity of the excitation radiation (profile progression) at the first excitation wavelength is shown in diagram A corresponding to the relative wave number 0 $cm^{-1}$. Furthermore, the filter characteristic of a first filter element 52 and a second filter element 52' is shown. The first filter element 52 has a transmission of 1.0 at a first filter wavelength, which has a spectral distance with a relative wave number of 100 $cm^{-1}$ to the first excitation wavelength, in a spectral range comprising a relative wave number of 10 $cm^{-1}$. Anywhere else in the shown range, the first filter element 52 completely blocks incident radiation. The second filter element 52' exhibits an identical filter characteristic, but at a second filter wavelength which has a spectral distance with a relative wave number of 120 $cm^{-1}$ to the first excitation wavelength.

If, in accordance with the representation in diagram A, excitation radiation of the first excitation wavelength is inelastically Raman-scattered by a specific sample element (for example at a first position of an optical setup according to the invention), then a Raman radiation corresponding to the first filter wavelength is within the passband of the first filter element 52 and becomes transmitted. A first detector arranged behind the first filter element 52 can thus determine the intensity of the scattered radiation at the first filter wavelength. However, the spectral width of the Raman-scattered radiation is too small to generate a corresponding intensity signal even on a second detector also after filtering through the second filter element 52' at the second filter wavelength. Thus, in the configuration shown in diagram A, a Raman line can be concluded at a relative wave number of 100 $cm^{-1}$. The width of the corresponding Raman line can be estimated in particular from the line width of the excitation radiation, the individual filter bandwidths of the filter elements (or their respective filter characteristics), as well as from the intensity ratio determined via the detectors.

In diagram B, the case is shown that excitation radiation of a second excitation wavelength, which has a spectral distance with a relative wave number of 20 $cm^{-1}$ to the first excitation wavelength $\lambda_1$, is also inelasticly Raman-scattered by the same sample element (for example, at a second position of an optical setup according to the invention). Since in this example the spectral distance between the two filter wavelengths of the two filter elements 52, 52' exactly corresponds to the spectral distance between the two excitation wavelengths of the excitation radiation (relative wave number difference of 20 $cm^{-1}$), only the intensity values determined via both detectors are interchanged. As a result, the occurrence of a corresponding Raman line presumed to be in accordance with diagram A can be confirmed. The spectral resolution and the reliability of examinations can be further increased by the irradiation of excitation radiation of several excitation wavelengths according to the invention and a corresponding filtering by a plurality of filter elements at different transmitted filter wavelengths. In particular, sample elements can be examined for the appearance of a plurality of Raman lines.

REFERENCE LIST 10 excitation source
12 excitation radiation (propagating in a first direction)
14 excitation radiation (propagating in a second direction)
16 deflecting mirror
18 beam splitter
20 Beam Dump
30 Flow volume
32 sample element
40 collecting optical system
50 beam splitter
52 first filter element (filter wavelength $\lambda_F$)
52' second filter element (filter wavelength $\lambda_{F'}$)

62 first detector (filter wavelength $\lambda_F$)
62' second detector (filter wavelength $\lambda_{F'}$)
100 Optical system
A first position
B second position
C-ZZ other positions
$\lambda_1$ first excitation wavelength
$\lambda_2$ second excitation wavelength
$f_1$ first filter wavelength
$f_2$ second filter wavelength
I first intensity (excitation wavelength $\lambda_1$ or $\lambda_2$, filter wavelength $f_1$ or $f_2$)
I' second intensity (excitation wavelength $\lambda_1$ or $\lambda_2$, filter wavelength $f_1$ or $f_2$)
O beam axis
L longitudinal axis
$\Delta z$ distance

What is claimed is:

1. An optical system comprising:
    a multispectral excitation source, designed to emit monochromatic excitation radiation successively at least two different excitation wavelengths along a common beam axis onto a sample element, wherein the multispectral excitation source switches between the at least two excitation wavelengths;
    an elongated flow volume with a longitudinal axis adapted to direct a particle flow along the longitudinal axis;
    an excitation beam path, designed to irradiate the monochromatic excitation radiation into the flow volume at a first position and a second position, wherein the first position and the second position are located in the elongated flow volume and the first position is spaced apart from the second position; and
    a detection device comprising a filter and a detector, the detection device designed to wavelength-selectively filter and detect at least one portion of a radiation scattered from the first position at a first filter wavelength and to wavelength-selectively filter and detect at least one portion of a radiation scattered from the second position at a second filter wavelength.

2. The optical system according to claim 1, further comprising a collecting optical system comprising a lens, the optical system designed to collect a radiation which is essentially scattered from the first position and to collect a radiation which is essentially scattered from the second position, and to direct the collected radiation onto the detection device.

3. The optical system according to claim 1, wherein the elongated flow volume has a tubular cross-section.

4. The optical system according to claim 1, wherein the excitation beam path is designed to irradiate into the elongated flow volume at least at the first position with the monochromatic excitation radiation at a first excitation wavelength and to irradiate into the flow volume at least at the second position with the monochromatic excitation radiation at a second excitation wavelength.

5. The optical system according to claim 1, wherein transmitted filter wavelengths of individual filter elements differ both from one another and also from individual excitation wavelengths of the monochromatic excitation radiation.

6. The optical system according to claim 1, wherein a radiation transmitted at transmitted filter wavelengths of individual filter elements is respectively detected by an individually assignable detector, and at least one first intensity and one second intensity for each excitation wavelength can be determined.

7. The optical system according to claim 1, wherein the detection device determines a Raman spectrum from at least two determined intensities.

8. The optical system according to claim 1, wherein a spectral distance between at least one excitation wavelength of the multispectral excitation source and a filter wavelength of a filter element corresponds to a Raman shift of the monochromatic excitation radiation, scattered by a sample element.

9. The optical system according to claim 2, wherein the detection device comprises at least one beam splitter, at which the radiation collected by the collecting optical system is divided into at least two beam paths, wherein a wavelength-selective filtering in a first beam path by a first filter element at a filter wavelength is performed and a wavelength-selective filtering in a second beam path by a second filter element at a second filter wavelength is performed.

10. The optical system according to claim 1, wherein the multispectral excitation source switches between the two excitation wavelengths in dependence on the position of a sample element along the longitudinal axis of the flow volume.

11. The optical system according to claim 2, wherein the collecting optical system comprises a positionally variable objective lens.

12. The optical system according to claim 1, wherein the multispectral excitation source comprises a Y-branch DBR-RW diode laser.

13. A method for spectroscopy comprising:
    flow transporting a sample element along a longitudinal axis of an elongated flow volume from a first end of the elongated flow volume to a second end of the elongated flow volume;
    irradiating the sample element with monochromatic excitation radiation of a first excitation wavelength of an excitation source at a first position along the longitudinal axis of the flow volume;
    switching from the first excitation wavelength of the excitation source to a second excitation wavelength of the excitation source, if the sample element is located in a range between the first position and a second position along the longitudinal axis of the flow volume; and
    irradiating the sample element with monochromatic excitation radiation of the second excitation wavelength of the excitation source at a second position along the longitudinal axis of the flow volume, wherein the second excitation wavelength is emitted along a common beam axis with the first excitation wavelength.

14. The method according to claim 13, further comprising:
    wavelength-selective filtering of the monochromatic excitation radiation, scattered by the sample element, of the first excitation wavelength of the excitation source by a first filter element and at least one second filter element, wherein a first transmitted filter wavelength of the first filter element and a second transmitted filter wavelength of the second filter element differ from the first excitation wavelength; and
    wavelength-selective filtering of the monochromatic excitation radiation, scattered by the sample element, of the second excitation wavelength of the excitation source by a first filter element and at least one second filter element, wherein a first transmitted filter wavelength of the first filter element and a second transmitted filter wavelength of the second filter element differ from the second excitation wavelength.

15. The method according to claim 13, wherein a radiation transmitted at transmitted filter wavelengths of individual filter elements is respectively detected by an individually assigned detector, and at least one first intensity and one second intensity for each excitation wavelength is determined.

16. The method according to claim 13, wherein a Raman spectrum is determined from at least two specific intensities.

17. The method according to claim 13, wherein a spectral distance between at least one excitation wavelength of the excitation source and one filter wavelength of a filter element corresponds to a Raman shift of an excitation radiation, scattered by a sample element.

18. The method according to claim 13, wherein the position of the sample element, flowing along the longitudinal axis of the flow volume, is determined.

* * * * *